United States Patent [19]
Kroll et al.

[11] Patent Number: 5,718,718
[45] Date of Patent: Feb. 17, 1998

[54] METHOD AND APPARATUS FOR POLARITY REVERSAL OF CONSECUTIVE DEFIBRILLATION COUNTERSHOCKS HAVING BACK BIASING PRECHARGE PULSES

[75] Inventors: Mark W. Kroll; Kai Kroll, both of Minnetonka, Minn.

[73] Assignee: Angeion Corporation, Plymouth, Minn.

[21] Appl. No.: 610,382

[22] Filed: Mar. 4, 1996

Related U.S. Application Data

[63] Continuation-in-part of Ser. No. 523,718, Sep. 5, 1995, abandoned, which is a continuation-in-part of Ser. No. 119,487, Sep. 13, 1993, abandoned.

[51] Int. Cl.$^6$ ........................................... A61N 1/39
[52] U.S. Cl. ........................................................ 607/5
[58] Field of Search ............................................ 607/5

[56] References Cited

U.S. PATENT DOCUMENTS

| | | |
|---|---|---|
| 4,637,397 | 1/1987 | Jones et al. . |
| 4,708,145 | 11/1987 | Tacker, Jr. et al. . |
| 4,727,877 | 3/1988 | Kallok . |
| 4,800,883 | 1/1989 | Winstrom . |
| 4,830,006 | 5/1989 | Haluska . |
| 4,850,357 | 7/1989 | Bach, Jr. ................ 607/74 |
| 4,953,551 | 9/1990 | Mehra et al. . |
| 5,052,407 | 10/1991 | Hauser et al. . |
| 5,107,834 | 4/1992 | Ideker et al. . |
| 5,133,353 | 7/1992 | Hauser . |
| 5,163,427 | 11/1992 | Keimel . |
| 5,184,616 | 2/1993 | Weiss . |
| 5,199,429 | 4/1993 | Kroll . |

(List continued on next page.)

FOREIGN PATENT DOCUMENTS 0280526  8/1988  European Pat. Off. .

OTHER PUBLICATIONS

U.S. application No. 08/523,718, Kroll et al., filed Sep. 5, 1995.

Electrode Polarity is an Important Determinant of Defibrillation Efficacy Using a Nonthroactomy System, Thakur et. al, PACE, vol. 17, May 1994, Part I, pp. 919–923.

Effect of Shock Polarity on Ventricular Defibrillation Threshold Using a Transvenous Lead System, Strickberger et al, JACC, vol. 24, No. 4, Oct. 1994, pp. 1069–1072.

Transvenous–Subcutaneous Defibrillation Leads: Effect of Transvenous Electrode Polarity on Defibrillation Threshold, Block et al, J of CE, vol. 5, No. 11, Nov. 1994, pp. 914–918.

The effect of polarity reversal on biphasic defibrillation threshold with an integrated transvenous lead system, Shorofksy et al, Circulation, vol. 90, No. 4, Part 2, Oct. 1994, p. 1224.

Medtronic® PCD™ Device Tachyarrhythmia Control System Reference Guide, Apr. 1992.

Ventritex® Cadence™ Tiered Therapy Defibrillator System Cadence Model V–100 and Cadence Programer, Preliminary Physician's Manual, Oct. 1990.

Ventak® PRx™ 1700/1705 Physician's Manual, Cardiac Pacemakers, inc.

*Primary Examiner*—William E. Kamm
*Attorney, Agent, or Firm*—Brad Pedersen

[57] ABSTRACT

A method and apparatus for controlling an implantable cardioverter defibrillator utilizes a back-biasing precharge circuit to precondition the heart before delivery of a biphasic electrical countershock. The back-biasing precharge circuit delivers a low voltage pulse to the implantable defibrillation electrodes that is opposite to the polarity of the initial phase of the biphasic countershock. In the event of a continuing cardiac arrhythmia which is not successfully converted by a single countershock, subsequent countershocks are delivered having alternating polarities from the preceding countershock such that both the polarity of the back-biasing pulse and the biphasic countershock are reversed as compared to the immediately preceeding countershock.

5 Claims, 10 Drawing Sheets

U.S. PATENT DOCUMENTS

| | | |
|---|---|---|
| 5,301,503 | 4/1994 | Martinelli . |
| 5,314,448 | 5/1994 | Kroll et al. .................................. 605/5 |
| 5,334,219 | 8/1994 | Kroll . |
| 5,336,484 | 8/1994 | Kroll . |
| 5,346,506 | 9/1994 | Mower et al. . |
| 5,385,574 | 1/1995 | Hauser et al. . |
| 5,395,394 | 3/1995 | Cameron . |
| 5,531,764 | 7/1996 | Adams et al. . |

METHOD AND APPARATUS FOR POLARITY REVERSAL OF CONSECUTIVE DEFIBRILLATION COUNTERSHOCKS HAVING BACK BIASING PRECHARGE PULSES

CROSS-REFERENCE TO RELATED APPLICATIONS

This application is a continuation-in-part application of Ser. No. 08/523,718, entitled "ELECTRODE BACK-CHARGING IMPLANTABLE CARDIOVERTER DEFIBRILLATOR", filed Sep. 5, 1995, now abandoned, which is a continuation-in-part of application Ser. No. 08/119,487, entitled "ELECTRODE BACK-BIASING IMPLANTABLE CARDIOVERTER DEFIBRILLATOR", filed Sep. 13, 1993, now abandoned, both of which are assigned to the assignee of the present invention, and the disclosure of each of which is herein incorporated by reference.

BACKGROUND OF THE INVENTION

1. Field of the Invention

The present invention relates to implantable cardioverter defibrillation systems. In particular, the present invention is an implantable cardioverter defibrillator system which delivers electrical countershocks of alternating polarity to a patient.

2. Background Information

Implantable cardioverter defibrillation (ICD) systems are well recognized and important tools managing the health of patients who have a history of heart problems. The typical ICD basically comprises a sealed housing which is implanted in the patient's body and contains various electronic components, and at least one lead/electrode which extends from the housing through the vascular system of the patient to the heart. Although much advancement has been made in ICD technology over the past several years, a remaining goal is to develop a smaller apparatus without sacrificing reliability. A smaller apparatus has obvious advantages in terms of patient comfort, ease of implantation, implantation location restrictions and other factors.

Defibrillation of the human heart is effected by passing a large current through the heart for a time period of several milliseconds (ms). A high voltage is generated by circuitry within the ICD housing and transmitted to the heart through the lead and electrodes. The magnitude of current that is required to successfully defibrillate the heart is related to the pulse width of the shock pulse. Since current is caused to flow by a high voltage stored on an energy or charge storage element, typically a capacitor, the impedance of the electrode path must be as low as possible. This is because current is related to voltage and resistance in accordance with Ohm's Law:

$$\text{Current} = \frac{\text{Voltage}}{\text{Resistance}}.$$

And, since voltage is determined by the maximum charge that the capacitor can store, the remaining critical variable in determining current flow for a given capacitor is resistance.

It is also the case that the energy of the defibrillation shock pulse sought to be delivered is the primary determinant of the size of the ICD device. This is because the largest component or components of the ICD are the charge storage capacitor(s) and their size is directly proportional to the energy that they must store. Typical ICD devices store approximately 1.77 joules (J) per cubic centimeter (cc) of volume. Thus, the size of the ICD device is a linear function of the energy required for defibrillation. The defibrillation shock energy is given electrically as:

$$\text{Energy} = IVd$$

where I is current, V is the voltage and d is the duration of the pulse. This formula is exact for rectangular pulses, but is also an accurate approximation when current and voltage vary during the pulse, as is the case with capacitive discharge. In such a case, "V" and "I" are average values. Taking into consideration Ohms Law the energy expression can be rewritten as:

$$E = I(IR)d.$$

From this relationship it can be seen that the required energy per pulse is proportional to the electrode resistance. This in turn implies that the size of the ICD device is a linear function of the electrode resistance. Accordingly, in order to accomplish the goal of ICD canister size minimization, while maintaining shock effectiveness, it is of extreme importance to keep the electrode resistance as low as possible.

There is a continuing need for an implantable cardioverter defibrillator which will reliably provide effective defibrillating shocks at the lowest defibrillation threshold possible. It would also be desirable to lower the energy required for providing the defibrillation shock which would allow ICD housing size to be reduced.

SUMMARY OF THE INVENTION

The present invention is an implantable therapy device capable of delivering a plurality of electrical biphasic countershocks to a patient's heart. The device has a housing which is implantable into a patient. Inside the housing is a battery and a charge storage device which are electrically connected to at least two implantable electrodes for applying a biphasic countershock to the patient's heart, and a control circuit which controls delivery of the biphasic countershocks. In the event of a continuing cardiac arrythmia which is not successfully converted by a single countershock, subsequent countershocks have alternating polarities as does an associated back biasing precharge applied the electrodes prior to each subsequent countershock.

There are no good theoretical models to explain why a given polarity of an electrical countershock delivered by an ICD might work better than others. It is entirely conceivable that the optimal polarity may vary over a period of time with the same patient. The ICD community cannot reach a consensus as to which polarity is most advantageous. The present invention eliminates the problems of having to test a patient and/or guess at which polarity would be best for that particular patient. Additionally, the present invention eliminates the chance of one polarity working well for the patient during testing, but not during an actual defibrillation episode.

The use of alternating polarities for a back biasing precharger allows the present invention to realize the polarity reversal at the electrodes between successive biphasic countershocks. Due to the fact that a biphasic countershock necessarily involves a polarity reversal as part of the countershock, the polarity at the electrodes naturally oscillates when two or more biphasic countershocks are delivered, however, the actual polarity of each phase of the countershock remains constant. The present invention avoids the problems of increased electrode resistance which would otherwise be present if the polarity of the phases of subsequent biphasic countershocks were to be reversed.

BRIEF DESCRIPTION OF THE DRAWINGS

FIG. 3b is a flow chart of the operation of the circuit in FIG. 3a.

FIG. 4a and b show real scaled and less scaled waveforms, respectively, of a representative defibrillation pulse delivered by the back biasing apparatus of FIG. 3.

DESCRIPTION OF THE PREFERRED EMBODIMENT

Figure 1:
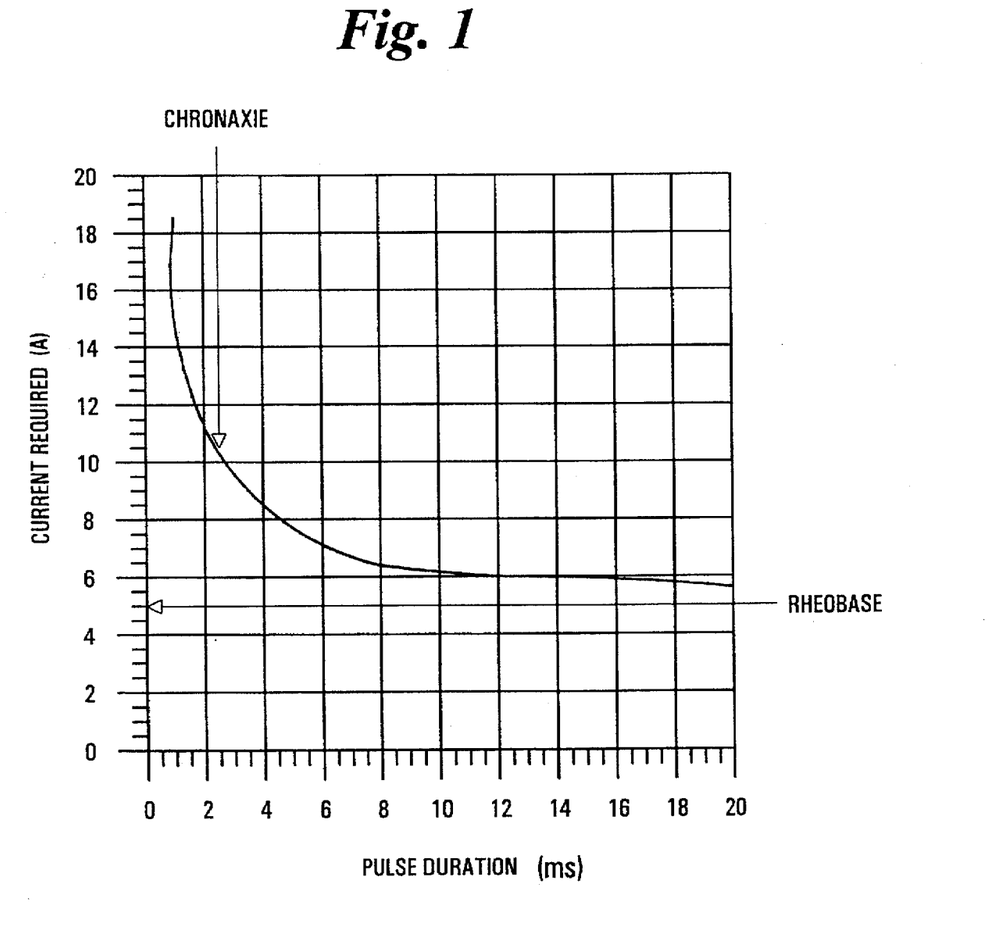
FIG. 1 is a graph showing a typical defibrillation strength-duration curve.

Defibrillation of the human heart is effected by passing a large current through the heart for a time period of several milliseconds (ms). A voltage is generated in the ICD housing and transmitted to the heart through the lead and electrodes. The magnitude of current that is required to successfully defibrillate the heart is related to the pulse width of the shock pulse. This is demonstrated in the "strength-duration" curve (S-D curve) for a typical patient as shown in FIG. 1. The S-D curve shows that in order to successfully defibrillate the exemplary heart with a given set of electrodes, an average current of 6 amps (A) is required for a pulse width of 12 ms, while an average current of 11.5 A is required for a pulse duration of 2 ms.

Figure 2A:
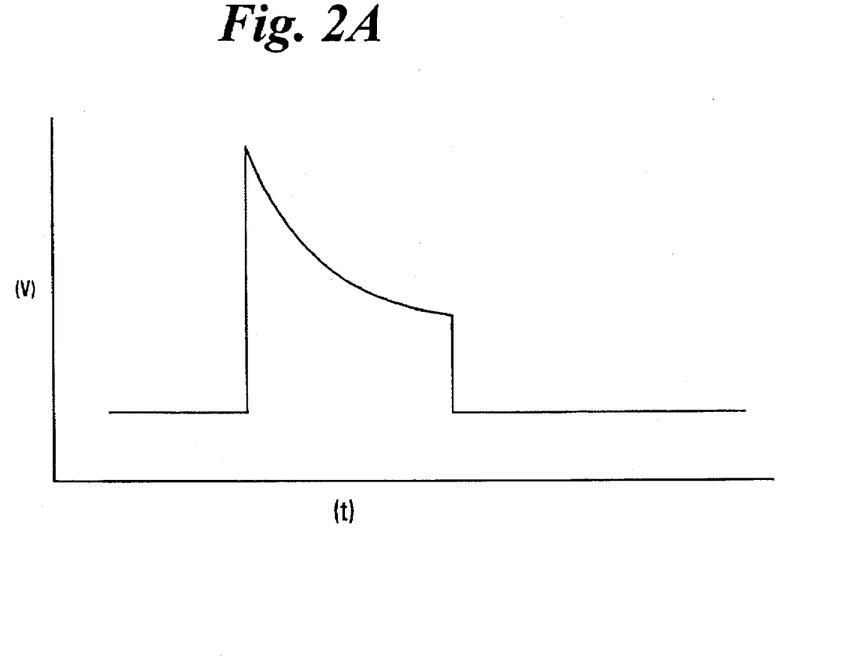
FIGS. 2a and b show typical monophasic and biphasic defibrillation waveforms.
Figure 2B:
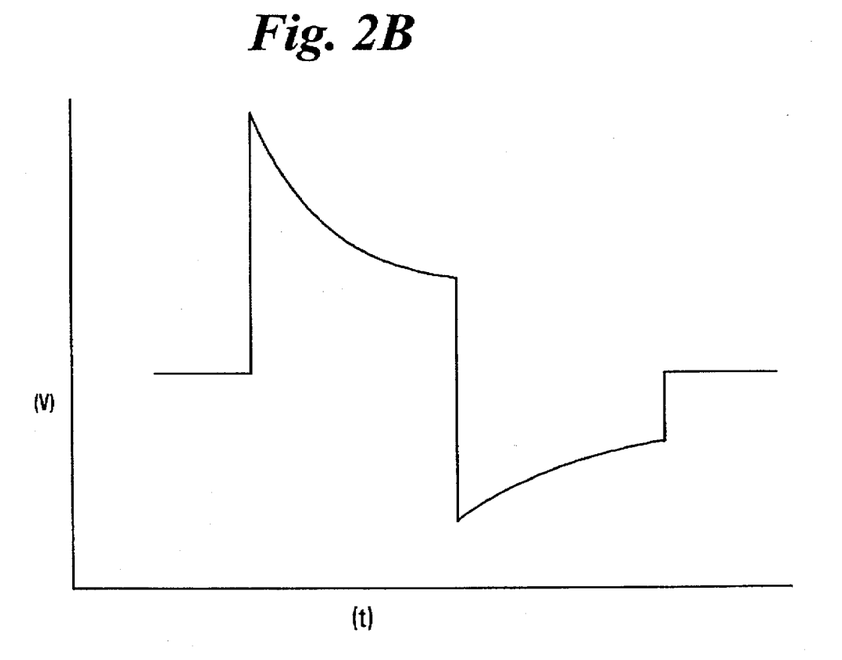

Existing ICD devices and methods deliver either a monophasic or biphasic defibrillation waveform to a patient's heart. A monophasic waveform is shown in FIG. 2a. In this case, an ICD capacitor is charged to a voltage of typically 650–750 V. The capacitor is then allowed to discharge through implanted defibrillation electrodes into the heart for a time period of approximately 6–12 ms. An alternative technique is the delivery of a biphasic waveform, an example of which is shown in FIG. 2b. In the case of the biphasic waveform, the capacitor is inverted in polarity with an "H-Bridge" switch, for example, to deliver current in a second phase in a polarity opposite to that of its first phase. This is continued for several additional milliseconds at which point the current flow is finally interrupted.

Figure 3A:
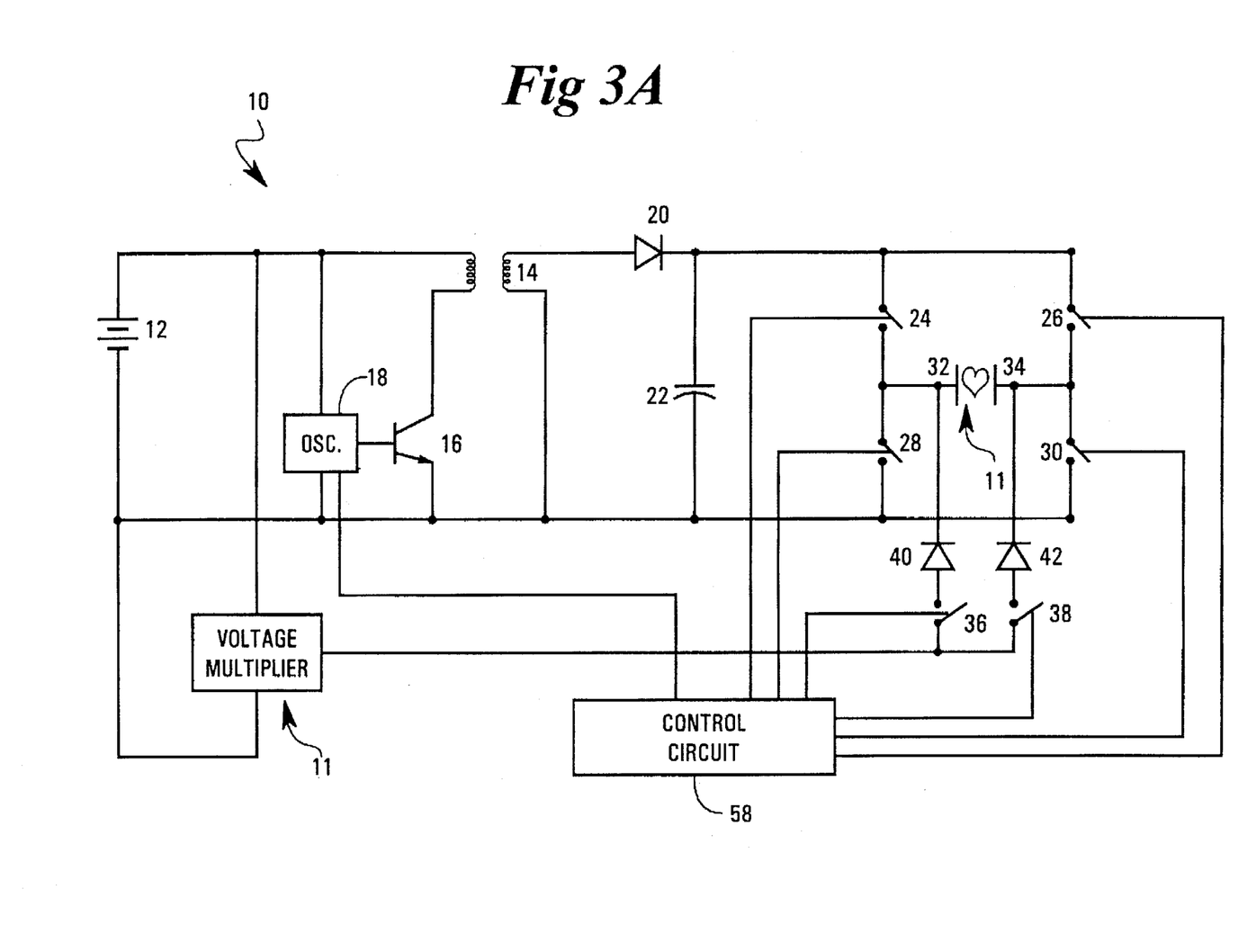
FIG. 3a shows a schematic circuit diagram of a back biasing apparatus.

Referring to FIG. 3a, an apparatus 10 for back-biasing an ICD is illustrated. The apparatus basically comprises a battery 12, a transformer 14, a transistor 16, an oscillator 18, a diode 20, a capacitor 22, and switches 24, 26, 28 and 30.

Electrodes 32 and 34 are preferably catheter-type electrodes known in the art and are inserted into the chambers of the heart. In the alternative, they may be patch style electrodes disposed on the exterior of the heart or the pericardium, or the device housing itself. Battery 12 is used to deliver a current through the primary of transformer 14 at a high frequency generated by transistor 16 and oscillator under control of a control circuit 58 18. This generates a high voltage at the secondary of transformer 14 which is rectified by diode 20 and stored in the main capacitor 22. Preferably, battery 12 generates a voltage of approximately 6V. A relatively small capacitor of approximately 60–100 microfarads (µF) may be used.

To deliver a monophasic pulse through the heart, switches 24 and 30 are turned on for approximately 3 milliseconds (ms) and then turned off. To deliver a biphasic waveform, switches 24 and 30 are turned on for 3 ms as is the case of a monophasic pulse, and then turned off. Switches 26 and 28 are then immediately turned on for approximately 3 ms to deliver a current in the opposite direction through the heart.

Importantly, the device 10 further comprises a voltage multiplier 11 which multiplies the battery voltage of approximately 6 V to a level of 12–18 V. Voltage levels up to 50V may be used, but they require more energy to perform the function more rapidly. This voltage is then delivered to either heart electrode 32 or 34 through additional switches 36 or 38 which are respectively in series with diodes 40 and 42. This voltage is delivered in a pulse of relatively low voltage and of relatively longer duration for back charging purposes as is described further below. All of the switches 24, 26, 28, 30, 36 and 38 are communicatively connected to and controlled by a control circuit (not shown) 58 of a design know in the art. It will be understood that the preferred embodiment of control circuit 58 will be a microcontroller operating under software program control to implement the mode of operation which is described for the present invention, although it would also be possible to implement the mode of operation of the present invention utilizing discrete logic components.

Figure 3B:
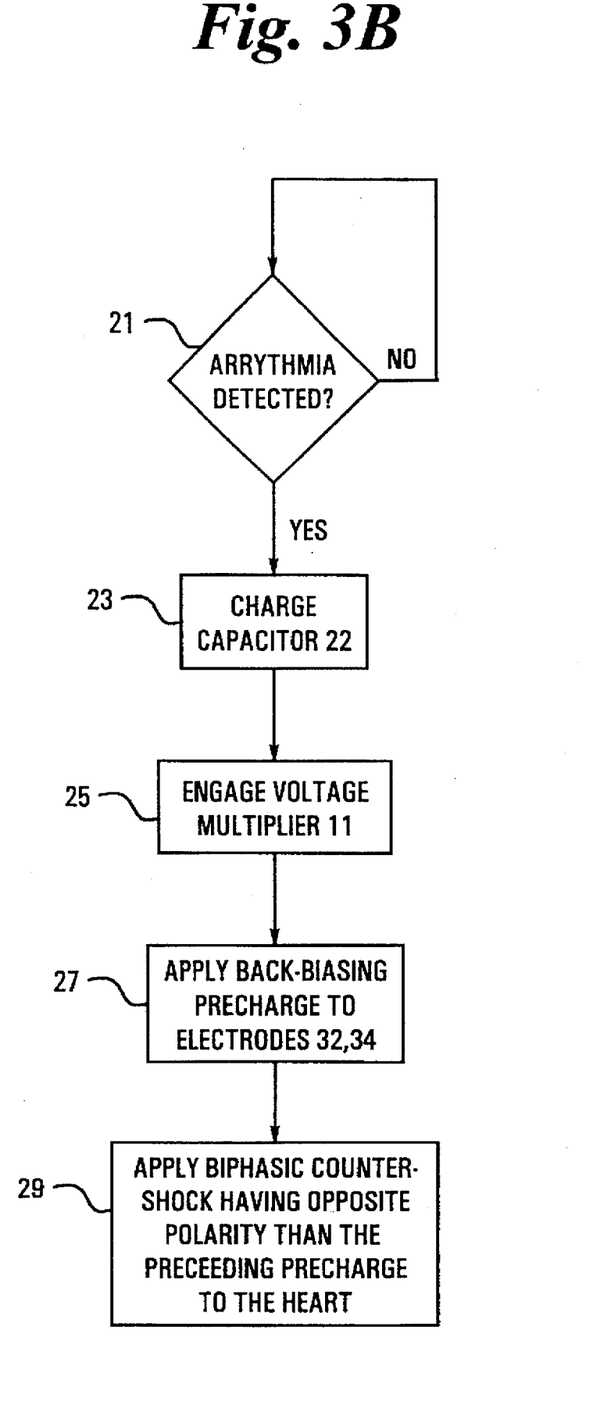

The mode of operation of apparatus 10 is as follows and is illustrated in FIG. 3b. After an arrhythmia is detected in block 21, the main capacitor 22 is charged up as indicated in block 23. While the main capacitor 22 is being charged, or during the end of such charging, or after such charging, voltage multiplier 11 is engaged to generate a voltage of preferably 12–18V. This is indicated in block 25. Switch 38 is turned on to deliver this low voltage to electrode 34. At the same time, switch 28 is turned on. This allows the flow of the relatively low voltage of 12–18V from voltage multiplier 11 through electrode 34, through electrode 32, through switch 28 and back to ground. This will deliver a small current flow through the heart, with a relatively long pulse duration of approximately 1 second in an opposite polarity to that of the yet-to-come defibrillation pulse. This back charges or pre-charges electrodes 32 and 34, as indicated in block 27.

Switches 28 and 38 are then opened and switches 24 and 30 are turned on. This delivers the high voltage, high current, short duration defibrillation shock (approximately 750V, 5 ms), through the heart from electrodes 32 and 34 as indicated in block 29. Importantly, the first phase of this biphasic shock is of opposite polarity to that of the current that was delivered for the back charging of electrodes 32 and 34. The polarity of the defibrillation pulse is defined as that of the first voltage phase.

Because the defibrillation shock is delivered with a polarity opposite to that of the back charging flow there is a reduced impedance and more current will pass through the heart. This results in increased efficiency of defibrillation for a given amount of energy and thus charge storage capacity. And since charge storage capacity is directly related to ICD size, a smaller, more compact ICD 10 is provided. The back charge voltage does not influence cardiac function significantly. The advantages of the reversed impulse are extended in those situations where multiple countershocks are necessary to treat a continuing arrythmia. In such a case, the present invention reverses the polarity of the back biasing exchange and the polarity of the subsequent biphasic countershock, as shown for example in FIG. 8.

Figure 6:
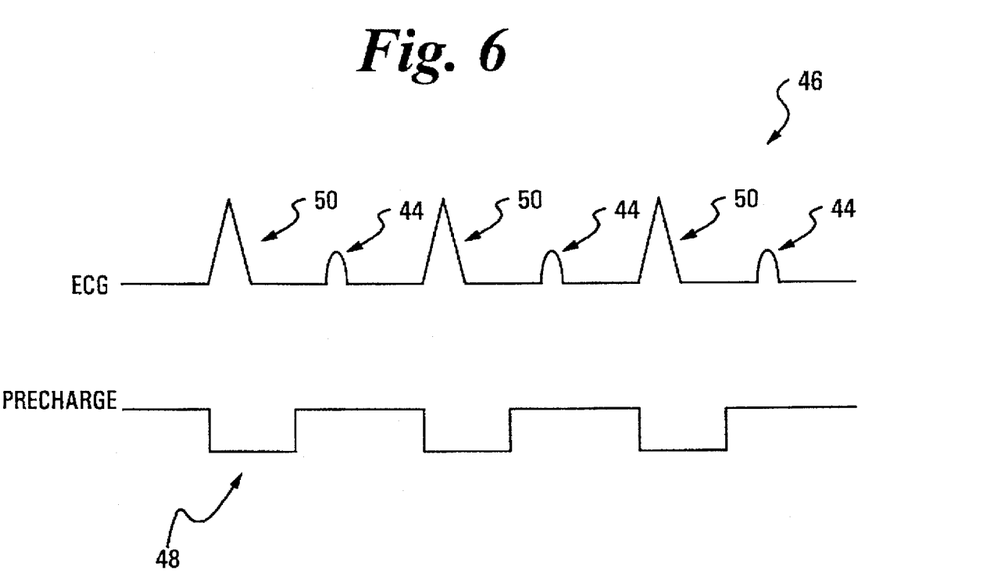
FIG. 6 is a graph showing an exemplary electrogram of cardiac function and an alternative back charge shock sequence.
Figure 7:
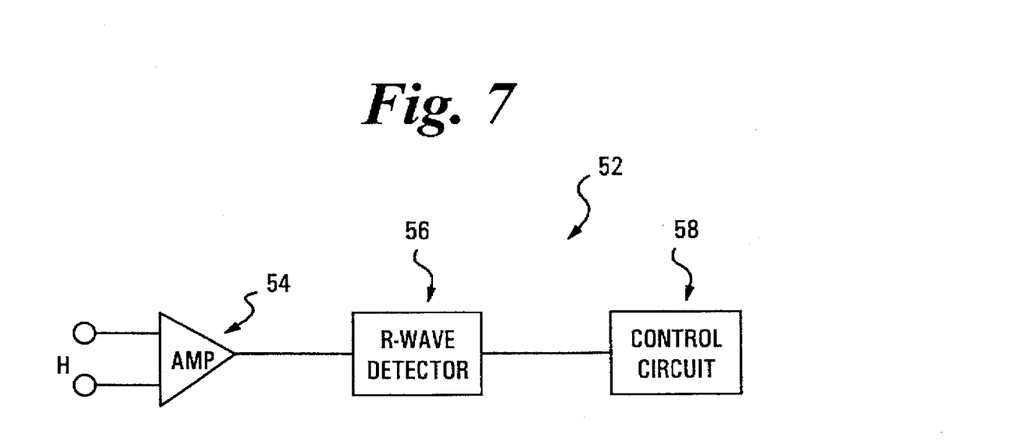
FIG. 7 is a schematic circuit diagram showing an alternative embodiment of the apparatus of FIG. 3.

An alternative embodiment of a back-biasing apparatus is shown in FIGS. 6 and 7. In a case where a patient is in a ventricular tachycardia (VT) rather than a ventricular fibrillation (VF), the application of a back charging precharging current may cause a ventricular fibrillation by stimulating the heart during the sensitive T-wave region 44 of an electrogram 46. Therefore, in such a case, a back charge current 48 is preferably delivered for only 100 ms after the start of the R-wave region 50 to avoid T-wave region 44. Apparatus 52 basically comprises, in addition to the elements described above in the main apparatus embodiment 10, an amplifier 54 connected to the heart, an R-wave detector 56 connected to amplifier 54, and an ICD control circuit 58 which is in turn connected to the remaining portion of the ICD as shown in FIG. 3a. It will be understood that in this embodiment control circuit 58 will include appropriate algorithms to distinguish between VT and VF utilizing any of a number of known techniques in the prior art.

Figure 4:
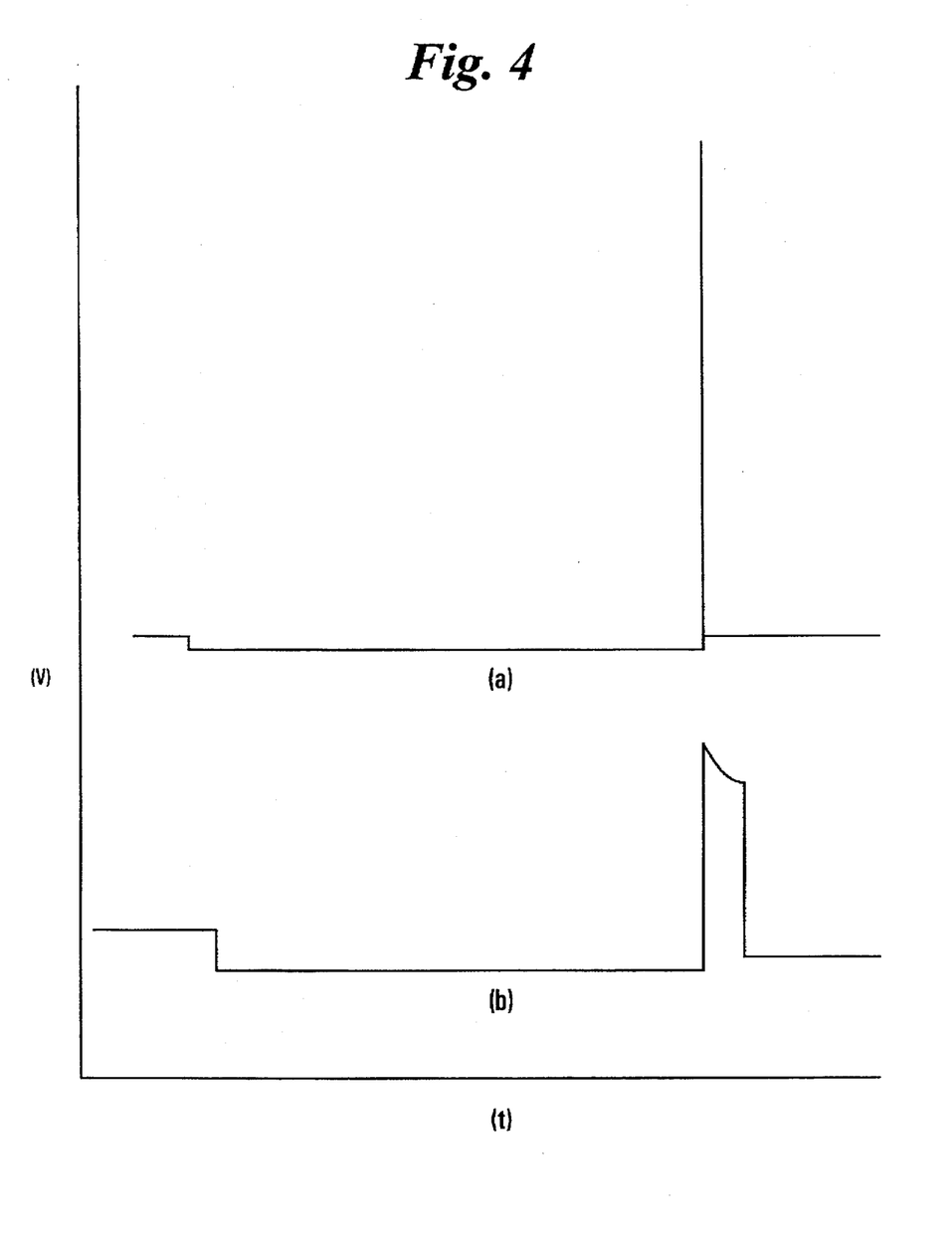

Exemplary defibrillation waveforms are shown in FIGS. 4 for a monophasic pulse. FIG. 4a shows the waveform in approximately real scaling. The long negative low voltage is approximately 1–2 seconds long in duration with potential of a negative 18V. The main defibrillation pulse lasts only several milliseconds (i.e., about 1,000th as long) but has an amplitude of around 700V. FIG. 4b shows the pulse in a more illustrative and less scaled fashion. Here the low voltage back charging pulse is shown preceding the main defibrillation pulse.

Figure 5:
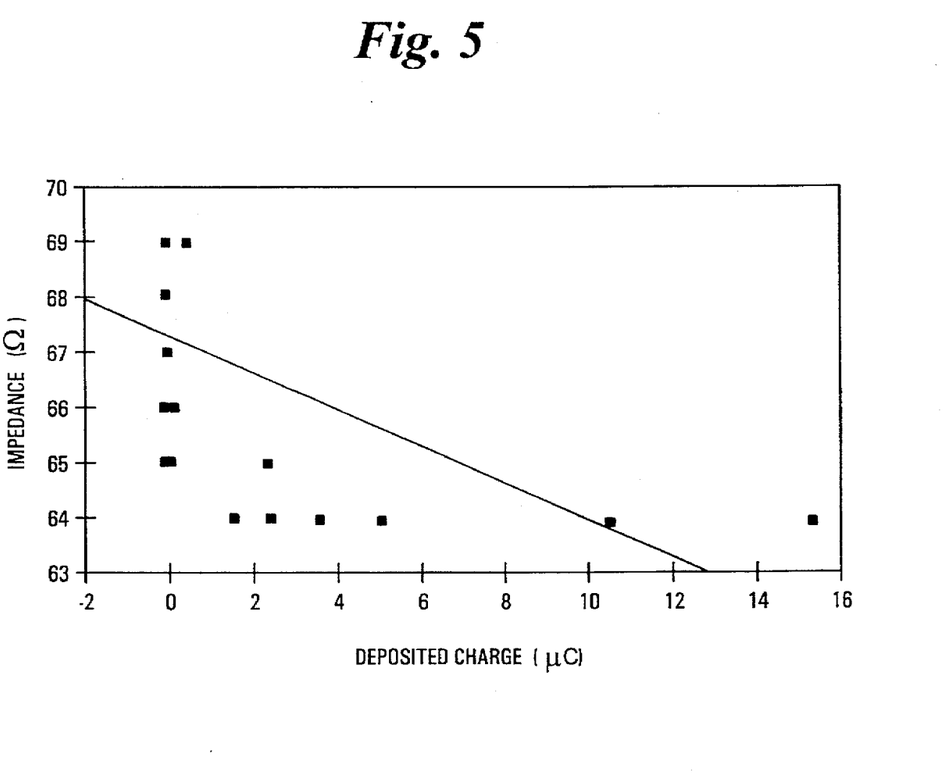
FIG. 5 is a graph showing the effect of shocks delivered by the apparatus of FIG. 3 in terms of impedance and charge (coulombs).

The effects of back charging an electrode pair are shown in the graph of FIG. 5. Here, the back charging is quantified by the charge in coulombs. The coulomb is a unit of charge equal to approximately 1/100,000 of a mole of electrons. It is given electronically as the product of the current and the time. In other words, a current of 1 amp is 1 coulomb flow per second. It should be noted that the impedance in the electrode pair was found to vary from 69 ohms down to 64 ohms with the lower impedance found after a back charging charge of at least 1 coulomb. The example represented in FIG. 5 is based on electrodes constructed of a stainless steel alloy known as MP-35 which is commonly used in defibrillation catheters. The reduction in impedance from 69 to 64 ohms, a reduction of 7 percent, directly translates into a reduction in necessary shock energy of 7 percent. In summary, the delivery of the low voltage, long duration back charging voltage pulse, which is of opposite polarity to that of a subsequently delivered defibrillation countershock, reduces physiological electrode path impedance and increase efficiency of defibrillation for a given amount of energy.

A major mechanism at work in back charging or precharging is the charging of the Helmholtz double layer capacitor. This mechanism basically holds that when an electrode disposed in bodily fluids is charged with a positive voltage it will repel the positively charged sodium ions in a nearby vicinity. The sodium ions cannot move very far away from the electrode as space charge neutrality must be maintained in the fluid in general. This space charge neutrality attempts to force the sodium ions back close to the electrode. The balancing distance is very small and this results in a Helmholtz capacitance. Similarly, the chlorine ions form a Helmholtz capacitance of the negative electrode. In the back-biasing apparatus described above, the Helmholtz capacitance can be charged by back charging the electrodes. An additional mechanism present, may be an electrochemical reaction at the electrodes, for example, the formation of a titanium oxide.

The present invention provides a method of treatment in which successive biphasic countershocks delivered in a therapy regimen are forced to alternate polarity. By forcing successive biphasic countershocks to alternate polarities approximately half of the countershocks received by the patient will be of the preferred polarity because as described above in the background section it is not a certainty which polarity is going to work better for any given patient, or, for that matter, for the same patient on any given day. Additionally, the present invention provides that prior to applying each biphasic countershock, a back charging pulse of opposite polarity to the up coming countershock is applied which will reduce the impedance, which in turn translates into an energy reduction.

Figure 8:
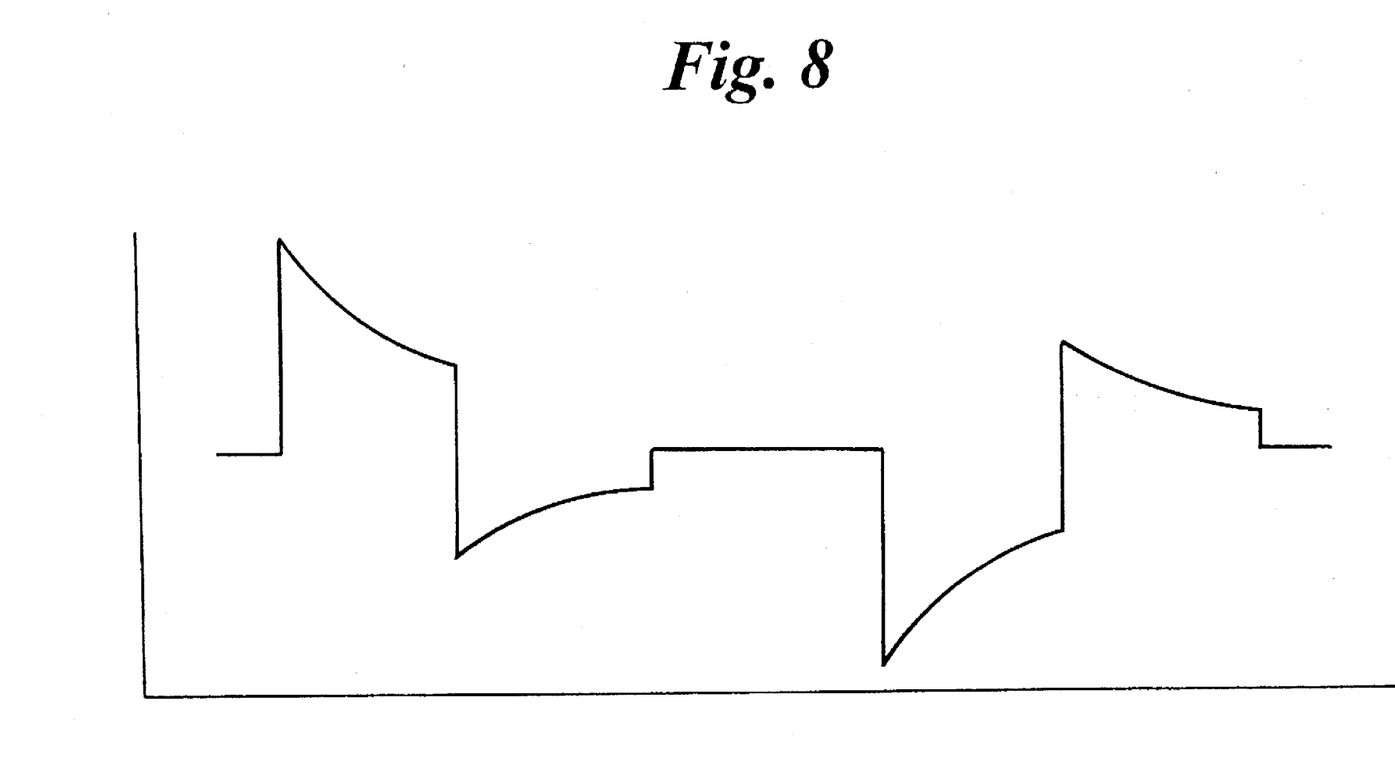
FIG. 8 shows successive biphasic waveforms forced to alternate polarity.

The circuit for the present invention is the same as that in FIG. 3 Generation of successive biphasic waveforms having alternate polarity is controlled by control circuitry 58 as shown in FIG. 3a. An illustration of successive biphasic waveforms having alternate polarities according to the present invention is illustrated in FIG. 8.

As stated in the background section, there are no good theoretical models to explain why a given polarity might work better than others. It is entirely conceivable that the optimal polarity may vary over a period of time with the same patient. The ICD community cannot reach a consensus as to which polarity is most advantageous. The present invention eliminates the problem of having to test a patient and/or guess at which polarity would be best for that particular patient. Additionally, the present invention eliminates the chance of one polarity working well for the patient during testing, but not during an actual defibrillation episode.

Figure 9:
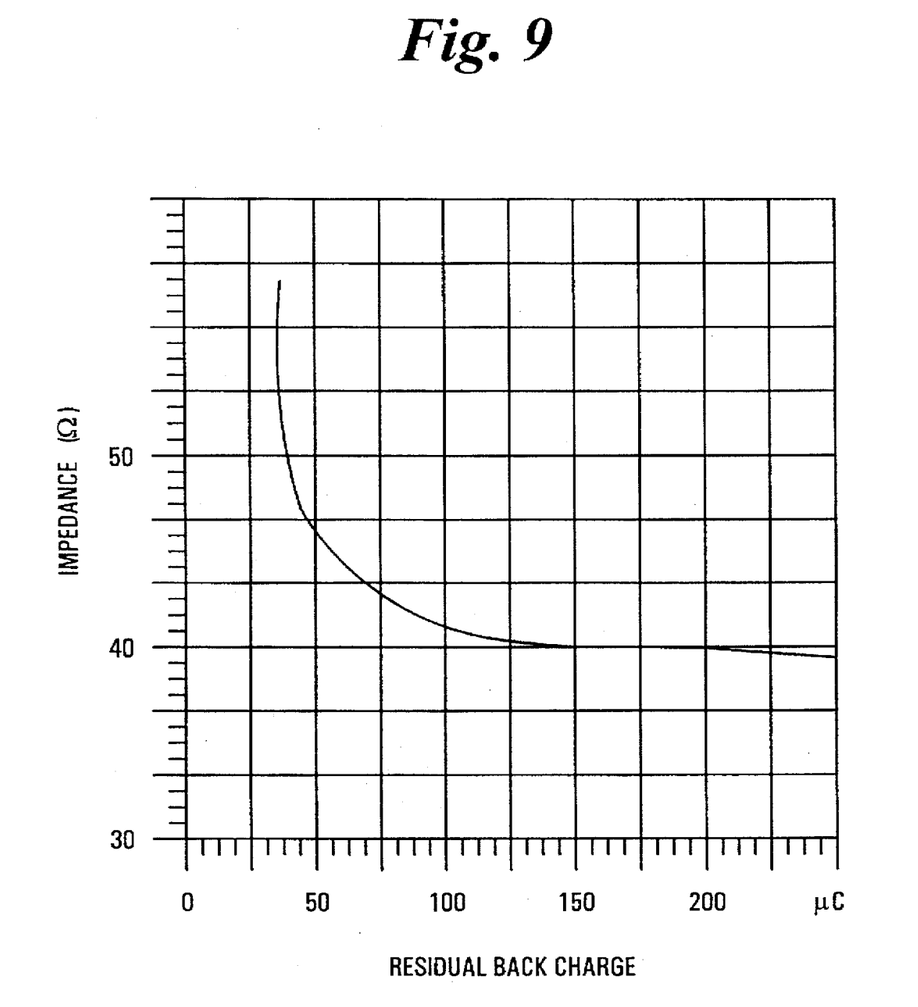
FIG. 9 illustrates the approximate relationship between the impedance and the residual back charge.

The description above related to back-biasing ICD's has demonstrated that precharging, or back-biasing, an electrode can significantly, under some circumstances, reduce the impedance. The passage of a reverse current through the electrodes deposits a charge. Due to the capacitive effect of that charge, and the high rise time of a following defibrillation shock, the net average impedance can be significantly lowered. The current is an important parameter in the defibrillation of the heart. For a given current, the voltage is proportional to resistance. The total energy requirements are proportional to the current multiplied by the voltage and thus any additional resistance translates linearly into additional energy. FIG. 9 illustrates the approximate relationship between the impedance and the residual back charge.

The present invention automatically alternates polarities between complete biphasic countershocks, such that the second phase of a first biphasic countershock will be of the same polarity as the first phase of a subsequent biphasic countershock. Thus, in order to reap the benefits of the precharging as discussed above, another precharge must be applied to the electrodes. This time, however, the precharge must be of an opposite polarity from that which was previously applied. As with changing the polarity of the biphasic countershocks, changing the polarity of the precharge is simply a matter of controlling switches 24, 26, 28, 30, 36 and 38.

Figure 10:
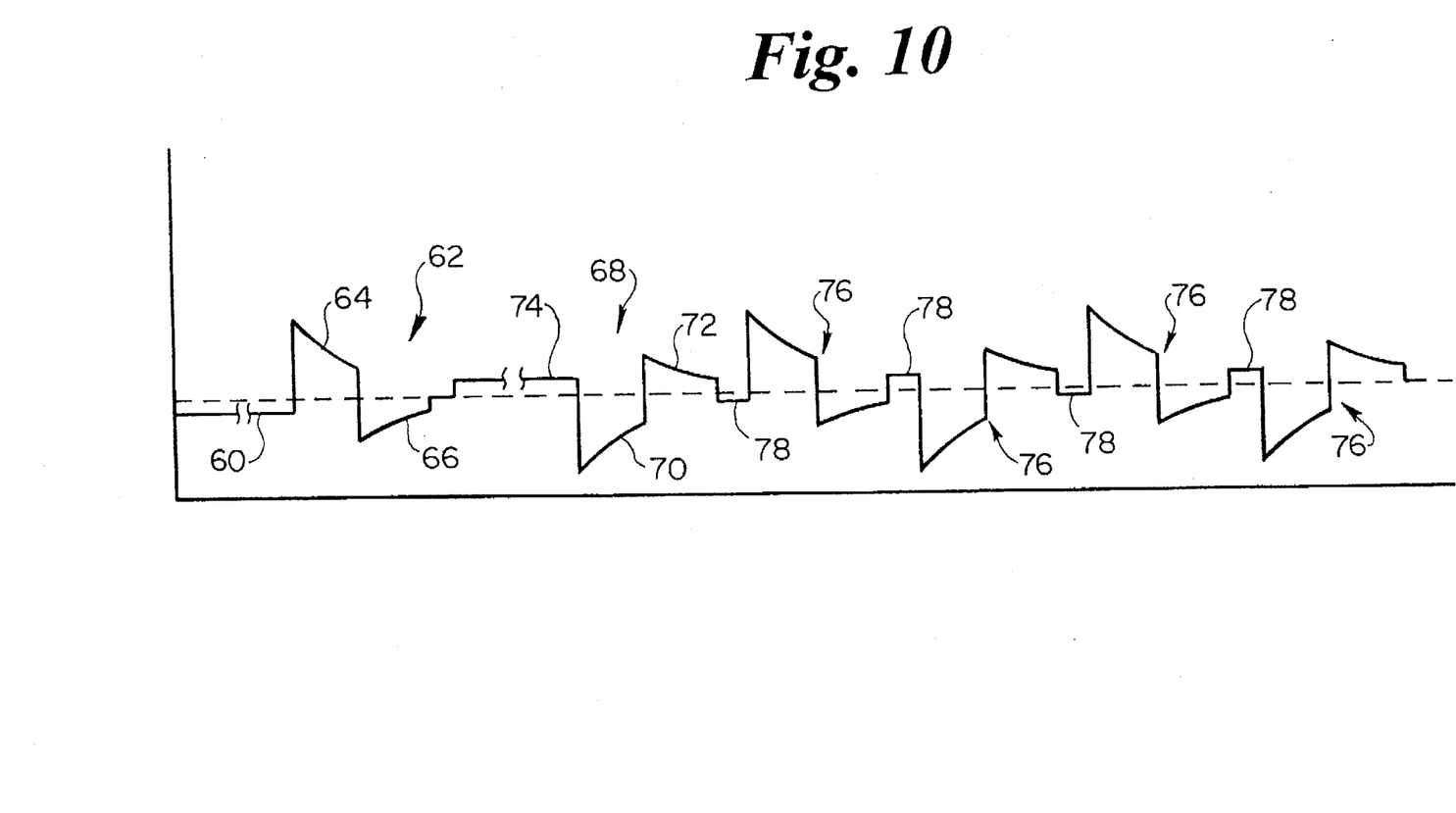
FIG. 10 illustrates an exemplary therapy regimen according to the present invention.

The polarity of the countershocks in the present invention are automatically alternated such that the patient will automatically receive countershock of both polarities in an attempt to convert a continuing arrythmia. Additionally, the countershocks have the advantages of the impedance reduction due to precharging. An exemplary therapy regimen is illustrated in FIG. 10. As illustrated in FIG. 10, a first precharging voltage 60 having a negative polarity is applied. A first biphasic countershock 62 comprising a first portion 64 and a second portion 66 is then applied to the patient's heart. First portion 64 has an absolute value of approximately 750 V and decays down to approximately 250 V over a period of 3–4 ms. The pulse then changes polarity and second portion 66 begins where first portion 64 left off, with an opposite polarity. Thus, second portion 66 has an initial absolute value of 250 V which decays down to approximately 150 V over a period of ms.

The system then pauses to see if normal sinus rhythm has been restored to the patient's heart. If not, a second biphasic pulse 68 having a first portion 70 being of a negative polarity, the opposite of first portion 64 of biphasic pulse 62, and a second portion 72 of positive polarity is applied to the heart. In order to obtain the benefits of the precharging, a precharge voltage 74 is again applied to the electrodes. Precharging voltage 74 is of a positive polarity because the first portion of the subsequent biphasic pulse is of a negative polarity. Precharging voltage 74 could be applied after a check has been done to see if normal sinus rhythm has been restored, or it could be applied while the system is checking for normal sinus rhythm.

After second biphasic countershock 38 has been applied, the system once again pauses to check to see if normal sinus rhythm has been restored. If not, a series of three to five additional biphasic countershocks are applied to the heart in rapid succession. These three to five biphasic countershocks are illustrated generally at 96 in FIG. 10 and as can be seen, they alternate polarities. Prior to the application of each of the biphasic countershocks, a precharging voltage 78 is applied to the electrodes in a polarity opposite to the first phase of the subsequent biphasic countershocks. It will be seen that precharging pulses 78 may be longer or shorter in duration as compared to those previously applied. Precharging pulses 60 and 74 may have a duration range from 0.1 to 10 s.

A therapy regimen such as that described above, and illustrated in FIG. 10 has both of the advantages discussed above. No matter which polarity shock works best for this patient at this time, the patient is going to receive a shock with the optimum polarity. If the first countershock works, then it must have been of the right polarity and further countershocks are not necessary. The second advantage obtained by this therapy regimen, is that because a precharging voltage is applied prior to the application of successively applied biphasic countershocks that alternate polarities, an energy reduction may be obtained.

We claim:

1. An implantable defibrillator system including a self-contained implantable device electrically connected to a plurality of implantable electrodes, the device comprising:

a sensing system that detects cardiac arrhythmias;

a charge storage system;

a battery system electrically connected to the charge storage system;

a switching system connected between the plurality of electrodes and the charge storage system and the battery system; and a control system connected to the sensing system, the charge storage system, the battery system and the switching system such that, in response to continued detection of a cardiac arrhythmia by the sensing system, the control system operates the battery system, the charge storage system and the switching system to deliver a series of electrical countershocks to the plurality of electrodes wherein each countershock includes a back biasing precharge pulse delivered from the battery system to the plurality of electrodes and having a biasing polarity followed by a biphasic pulse delivered from the charge storage system to the plurality of electrodes and having an initial polarity that is opposite to the biasing polarity, and wherein the biasing polarity of the back biasing precharge pulse and the initial polarity of the biphasic pulse are reversed for each consecutive electrical countershock in the series of electrical countershocks.

2. The system of claim 1 wherein the control system operates to deliver the back biasing precharge pulse as a single low voltage pulse having a duration of between 0.1 and 10 seconds.

3. The system of claim 1 further comprising a voltage multiplier connected between the battery system and the electrodes for increasing the voltage of the back biasing precharge pulse applied to the plurality of electrodes.

4. A method of defibrillating a human heart comprising the device-implemented steps of:

(a) monitoring cardiac activity;

(b) in response to detection of a cardiac arrhythmia delivering an initial electrical countershock to the heart by performing the steps of (b1) delivering a low voltage back biasing precharge pulse having a biasing polarity;

(b2) delivering a high voltage biphasic pulse having an initial polarity that is opposite to the biasing polarity, (c) monitoring cardiac activity to determine if the initial countershock was successful in converting the cardiac arrhythmia, and if unsuccessful, delivering a subsequent electrical countershock by performing the steps of:

(c1) delivering a low voltage back biasing precharge pulse having a biasing polarity;

((b2) delivering a high voltage biphasic pulse having an initial polarity that is opposite to the biasing polarity, wherein the biasing polarity of the back biasing precharge pulse and the initial polarity of the biphasic pulse of the subsequent countershock are reversed from the previous countershock.

5. The method of claim 4 further comprising the step of:

(d) repeating step (c) until the cardiac arrhythmia is converted or until a predetermined number of countershocks have been delivered.

* * * * *